(12) United States Patent
Miki et al.

(10) Patent No.: US 8,227,096 B2
(45) Date of Patent: Jul. 24, 2012

(54) ARYLAMINE COMPOUND AND ORGANIC ELECTROLUMINESCENCE DEVICE

(75) Inventors: Tetsuzo Miki, Minato-ku (JP); Norimasa Yokoyama, Tsukuba (JP); Yoshio Taniguchi, Ueda (JP); Musubu Ichikawa, Ueda (JP)

(73) Assignees: Hodogaya Chemical Co., Ltd., Tokyo (JP); Shinshu University, Matsumoto-shi (JP)

( * ) Notice: Subject to any disclaimer, the term of this patent is extended or adjusted under 35 U.S.C. 154(b) by 0 days.

(21) Appl. No.: 12/966,181

(22) Filed: Dec. 13, 2010

(65) Prior Publication Data

US 2011/0133171 A1 Jun. 9, 2011

Related U.S. Application Data

(63) Continuation of application No. 12/065,417, filed as application No. PCT/JP2006/317272 on Aug. 31, 2006, now Pat. No. 7,867,632.

(30) Foreign Application Priority Data

Aug. 31, 2005 (JP) ................................. 2005-251968

(51) Int. Cl.
    *H01L 51/54* (2006.01)
(52) U.S. Cl. ........ 428/690; 428/917; 313/504; 313/505; 313/506; 564/426; 564/434
(58) Field of Classification Search .................. 428/690, 428/917; 313/504, 405, 506; 564/426, 434
    See application file for complete search history.

(56) References Cited

U.S. PATENT DOCUMENTS

| 7,812,341 B2 | 10/2010 | Miki et al. |
| 2003/0219625 A1 | 11/2003 | Wolk et al. |
| 2007/0285004 A1 | 12/2007 | Miki et al. |
| 2009/0102361 A1 | 4/2009 | Miki et al. |
| 2010/0066244 A1 | 3/2010 | Miki et al. |

FOREIGN PATENT DOCUMENTS

| JP | 8 48656 | 2/1996 |
| JP | 8 259940 | 10/1996 |
| JP | 10-302960 | 11/1998 |
| JP | 3194657 | 6/2001 |

OTHER PUBLICATIONS

Shirota, A Novel Class of pi—Electron Dendrimers for Thermally and Morphologically Stable Amorphous Molecular Materials, 1998, Advanced Materials, pp. 223-226.*

Shirota, A Novel class of pi—electron dendrimers . . . , Advanced Materials, 1998, p. 223-226.
Yasuhiko Shirota, et al., "Charge Transport in Amorphous Molecular Materials", Proceedings of SPIE—The International society for optical Engineering (Organic Light-Emitting Materials and Devices IX), vol. 5937, pp. 593717-1-593717-10, 2005.
Katsuhiko Katsuma, et al., "A Novel Class of π-Electron Dendrimers for Thermally and Morphologically Stable Amorphous Molecular Materials", Advanced Materials, vol. 10. No. 3, pp. 223-226, 1998.
J. C. Carter, et al., "Operating Stability of Light-Emitting Polymer Diodes Based on Poly(P-Phenylene Vinylene)", Applied Physics Letters, vol. 71, No. 1, Pager 34-36, 1997.
Arjan Berntsen, et al., "Stability of Polymer LEDs", Optical Materials, vol. 9, pp. 125-133, 1998.
"Journal of Organic Molecular Electronics and Bioelectronics of Japan Society of Applied Physics, M&BE", vol. 11, No. 1, pp. 13-19, 2000.

* cited by examiner

*Primary Examiner* — Jennifer Chriss
*Assistant Examiner* — Gregory Clark
(74) *Attorney, Agent, or Firm* — Oblon, Spivak, McClelland, Maier & Neustadt, L.L.P.

(57) ABSTRACT

This invention relates to an arylamine compound having a molecular weight of 1,500 to 6,000 represented by formula (1), and to an organic electroluminescence device having a pair of electrodes and at least one organic layer sandwiched therebetween, wherein the arylamine compound of formula (1) is used as a constituting material of the at least one organic layer:

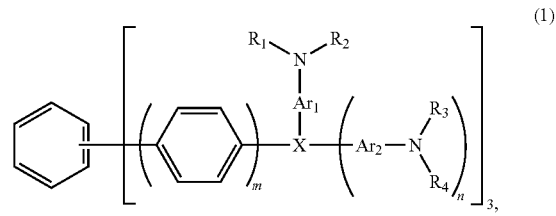

(1)

wherein X represents a single bond, CH or $CH_2$, or N or NH; $Ar_1$ and $Ar_2$ are respectively the same and each represents a substituted or unsubstituted phenylene group; $R_1$, $R_2$, $R_3$, and $R_4$ each independently represents an aryl group, wherein the aryl group may be substituted by a diarylamine group in such a manner as to form a triphenylamine partial structure, and the aryl group at the terminal may be substituted, by repetition, by a diarylamino group in such a manner as to form a triphenylamine partial structure; m represents an integer of 0 to 2; and n represents 0 or 1.

12 Claims, 2 Drawing Sheets

ARYLAMINE COMPOUND AND ORGANIC ELECTROLUMINESCENCE DEVICE

TECHNICAL FIELD

This invention relates to a compound suitable for an organic electroluminescence (EL) device which is a self-luminescent device suitable for various display apparatuses and to a device. More specifically, the invention relates to an arylamine compound having a molecular weight of 1,500 to 6,000 and to an organic EL device using a coated film layer of the compound.

BACKGROUND ART

Since the organic EL devices are self-luminescent devices, they are bright, excellent in visibility, and capable of giving clear display as compared to liquid crystal devices, and studies thereon have actively been conducted.

In 1987, C. W. Tang et al. of Eastman Kodak Co. have turned the organic EL device using an organic material into practical utilization by developing a multilayer device wherein various functions are respectively distributed to materials. They stack a fluorescent material capable of transporting electrons and an organic substance capable of transporting holes, and injected both of the charges into the fluorescent material layer to emit a light, thereby achieving a high luminance of 1,000 cd/m$^2$ or more at a voltage of 10 V or less (see Patent Document 1 and Patent Document 2, for example).

Patent Document 1: JP-A-8-48656
Patent Document 2: Japanese Patent No. 3194657

From differences in process of device preparation and characteristics of materials, the organic EL devices are classified into devices of vapor deposition type using a low molecular material and devices of wet-process type mainly using a polymer material.

The vapor deposition type device requires a vacuum vapor deposition apparatus for film formation. Contrary, in the case of the wet-process type device, film formation is easily carried out by coating a substrate with a coating liquid and then removing a solvent in the coating liquid. Therefore, the wet-process type device is obtainable by a simple production process and at a low production cost. Since the coating is easily performed by an ink jet method and a printing method, no expensive equipment is required for the production.

Polymer materials such as poly(1,4-phenylenevinylene) (hereinafter abbreviated as PPV) have generally been used as materials for the production of the wet-process type device (see Non-Patent Document 1, for example).

Non-Patent Document 1: Applied Physics Letters, 71-1, page 34, (1997)

Also, an organic EL device having a hole injection layer, a hole transport layer, and an electron transport layer in addition to an luminescent layer, thereby further segmentalizing various roles has been studied. Poly(ethylenedioxythiophene)/poly(styrenesulfonate) (hereinafter abbreviated as PEDOT/PSS) has widely been used as a hole injection or transport material for forming a hole injection layer or a hole transport layer by coating (see Non-Patent Document 2, for example).

Non-Patent Document 2: Optical Materials 9 (1998) 125

However, a coating liquid of PEDOT/PSS is an acidic aqueous solution since the coating liquid is an aqueous gel dispersion hydrated by PSS to which a molecular chain of PEDOT gives an ionic interaction. Therefore, the coating liquid has difficulties in use such as corrosion by the coating liquid of a coating/printing device such as an inkjet ejection head.

Also, it has been pointed out that PSS in the coating film adversely affects on an anode and that water used for the coating liquid remains in the device to result in deterioration during driving. Further, a thiophene ring in PEDOT is said to be reduced due to electron influx. Having these difficulties, PEDOT/PSS cannot be considered as a satisfactory hole injection/transport material, and satisfactory device characteristics were not obtained, particularly, in terms of durability.

As hole injection/transport materials other than PEDOT/PSS, polymers such as poly(N-vinylcarbazole) (hereinafter abbreviated as PVK) have been known (see Non-Patent Document 3, for example).

Non-Patent Document 3: Journal of Organic Molecular Electronics and Bioelectronics of Japan Society of Applied Physics, Vol. 11, No. 1, pages 13 to 19, (2000)

In the polymer materials including both PEDOT/PSS and PVK, there is a concern for influences caused by a low molecular material used for polymerization and crosslinking of the polymer. Also, since the polymer material in general is a mixture of various molecular species, the composition thereof is not perfectly uniform, thereby making it difficult to equalize the performance of devices produced.

In order to solve the above problems, Japanese Patent Application Nos. 2004-089836 and 2004-090334 propose an arylamine compound of a single molecular species and excellent in amorphousness and derivatives thereof, and also propose highly efficient and highly durable organic EL devices using a coated film layer of the these compounds.

Since a work function exhibited by these compounds is close to that of ITO, the compounds are suitably used as the hole injection material like PEDOT/PSS. However, in the case where the compounds are used singly as the hole injection/transport material, efficiency of an organic EL device was lower than that obtained by using PVK since the work function of the compound is low as the hole transport material.

A high performance amorphous material that is of a single molecular species and singly usable as a hole injection/transport material has not been obtained. Therefore, a highly efficient and highly durable organic EL device has not been obtained.

Meanwhile, JP-A-8-49045 has proposed an organic EL device using a compound having a structure similar to that of this invention. The invention proposes a production of an organic EL device having a high heat stability by using an arylamine compound characterized by having 3 or more anilinobenzene molecular structures bonded to a single molecule or by using a derivative thereof. However, since it is difficult to prepare a coating liquid from the compound having such structure due to its characteristic of being hardly soluble to organic solvents, a device production method thereof is a vapor deposition method.

DISCLOSURE OF THE INVENTION

Problems to be Solved by the Invention

An object of this invention is to provide a compound suitable for film formation by coating as a material for a highly efficient and highly durable organic EL device. Another object of this invention is to provide a compound of a single molecular species having excellent hole injection/transport property and excellent amorphousness.

Means to Solve the Problems

The inventors of this invention have explored compounds that are readily soluble to organic solvents and have a high work function and excellent amorphousness, conducted chemical syntheses of various compounds, experimentally produced organic EL devices, and compared characteristics evaluations of the devices. As a result of the extensive research, the inventors have found that the compound of this invention is a high performance hole injection/transport material, and that a highly efficient and highly durable organic EL device can be obtained by using the compound, thereby accomplishing this invention.

That is, this invention relates to an arylamine compound having a molecular weight of 1,500 to 6,000 represented by the general formula (1), and also relates to an organic electroluminescence device comprising a pair of electrodes and at least one organic layer sandwiched therebetween, wherein the compound is used as a constituting material of the at least one organic layer in the form of a coated film layer:

[Chem. 1]

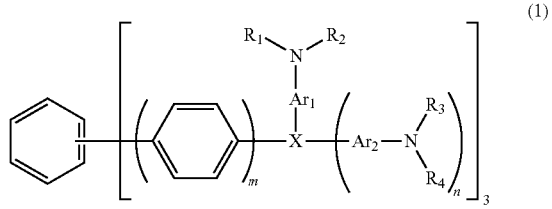

(1)

wherein X represents a single bond, CH or CH$_2$, or N or NH; Ar$_1$ and Ar$_2$ are respectively the same and each represents a substituted or unsubstituted phenylene group, biphenylene group, or terphenylene group; R$_1$, R$_2$, R$_3$, and R$_4$ each independently represents an aryl group, wherein the aryl group may be substituted by a diarylamine group in such a manner as to form a triphenylamine partial structure, and the aryl group at the terminal may be substituted, by repetition, by a diarylamino group in such a manner as to form a triphenylamine-like partial structure; m represents an integer of 0 to 2; and n represents 0 or 1.

Preferred among the arylamine compounds having a molecular weight of 1,500 to 6,000 represented by the general formula (1) are those having 6 or 9 nitrogen atoms in its molecule.

Preferred among the arylamine compounds having a molecular weight of 1,500 to 6,000 represented by the general formula (1) are those having in its molecule 6 to 9 triphenylamine-like partial structures in each of which a benzene ring and a benzene ring are bonded by a bonding group as in triphenylamine, a carbazole group, or the like.

Examples of the substituent group in the substituted phenylene group, the substituted biphenylene group or the substituted terphenylene group represented by Ar$_1$ and Ar$_2$ in the general formula (1) include an alkyl group, and a methyl group is preferred among others. Also, the phenylene group or the biphenylene group bonded to the central benzene ring of the arylamine compound represented by the general formula (1) may also be substituted by a similar substituent group.

Specific examples of the aryl group represented by R$_1$ to R$_4$ in the general formula (1) include a substituted or unsubstituted phenyl group, a substituted or unsubstituted biphenyl group, a substituted or unsubstituted naphthyl group, and a substituted or unsubstituted terphenyl group. Specific examples of the substituent group in the substituted phenyl group, the substituted biphenyl group, the substituted naphthyl group, and the substituted terphenyl group include a fluorine atom, a chlorine atom, a cyano group, a hydroxide group, a nitro group, an alkyl group, an alkoxy group, an amino group, a trifluoromethyl group, a naphthyl group, an aralkyl group, a fluorenyl group, an indenyl group, a pyridyl group, a pyrimidyl group, a furanyl group, a pyronyl group, a thiophenyl group, a quinolyl group, a benzofuranyl group, a benzothiophenyl group, an indolyl group, a carbazolyl group, a bezooxazolyl group, a quinoxalyl group, a bezoimidazolyl group, a pyrazolyl group, a dibenzofuranyl group, and a dibenzothiophenyl group. These substituent groups may be further substituted.

The arylamine compound having a molecular weight of 1,500 to 6,000 represented by the general formula (1) of this invention not only has an excellent hole injection/transport property, but also it enables easy formation of a stable thin film through coating. As a result, it has been proved that the compound enables realization of a highly efficient organic EL device.

The device using the arylamine compound having a molecular weight of 1,500 to 6,000 of this invention is free from a fear of anode deterioration otherwise caused by ion diffusion from a coating film and free from a fear of influences of moisture as seen in a device using PEDOT/PSS. Therefore, improvements in durability of the device are expected.

The organic EL device of this invention realizes high efficiency and high durability by the use of the arylamine compound having a molecular weight of 1,500 to 6,000, which has excellent hole injection/transport characteristics and is capable of forming a stabile thin film.

Advantage of the Invention

This invention relates to an arylamine compound having a molecular weight of 1,500 to 6,000, which is useful as a material for a thin film of a hole injection/transport layer of an organic EL device, and to an organic EL device produced using the compound. By this invention, luminescent efficiency and durability of conventional wet-process type organic EL devices can be dramatically improved.

BEST MODE FOR CARRYING OUT THE INVENTION

Figure 1:
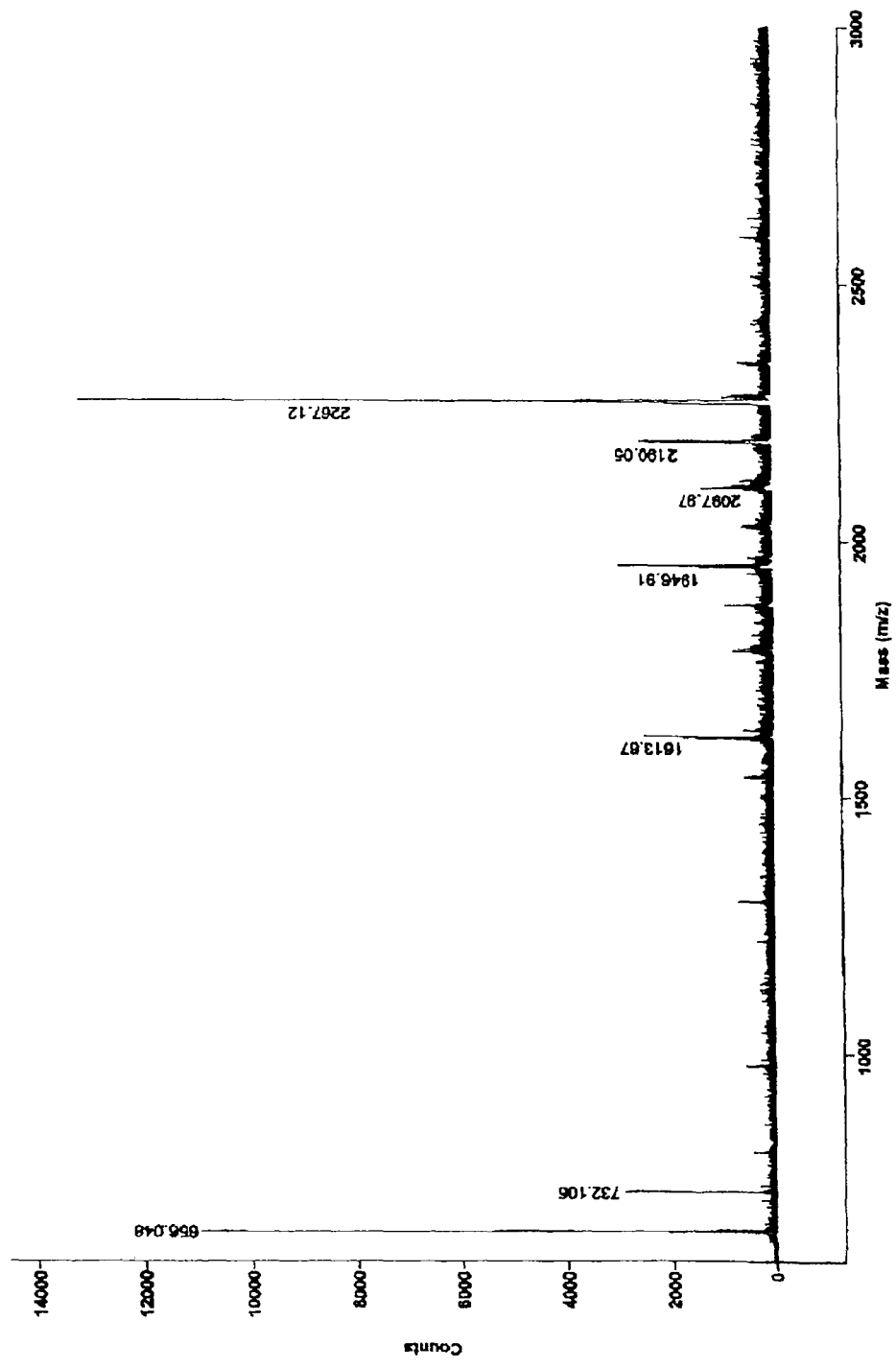
FIG. 1 is a chart of TOF-MS of TPA9-2.
Figure 2:
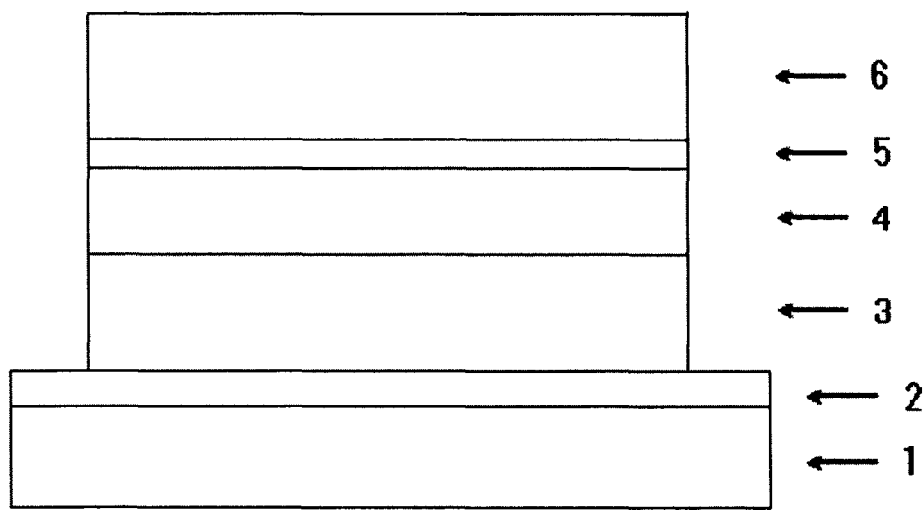
FIG. 2 is a diagram showing the EL device structure of Example 6.

The arylamine compound having a molecular weight of 1,500 to 6,000 of this invention can be synthesized by a condensation reaction such as the Ullmann reaction of corresponding arylamine and corresponding aryl halide.

Specific examples of preferred compounds among arylamine compounds represented by the general formula (1) are shown below, but this invention is not limited to the compounds.

[Chem. 2]
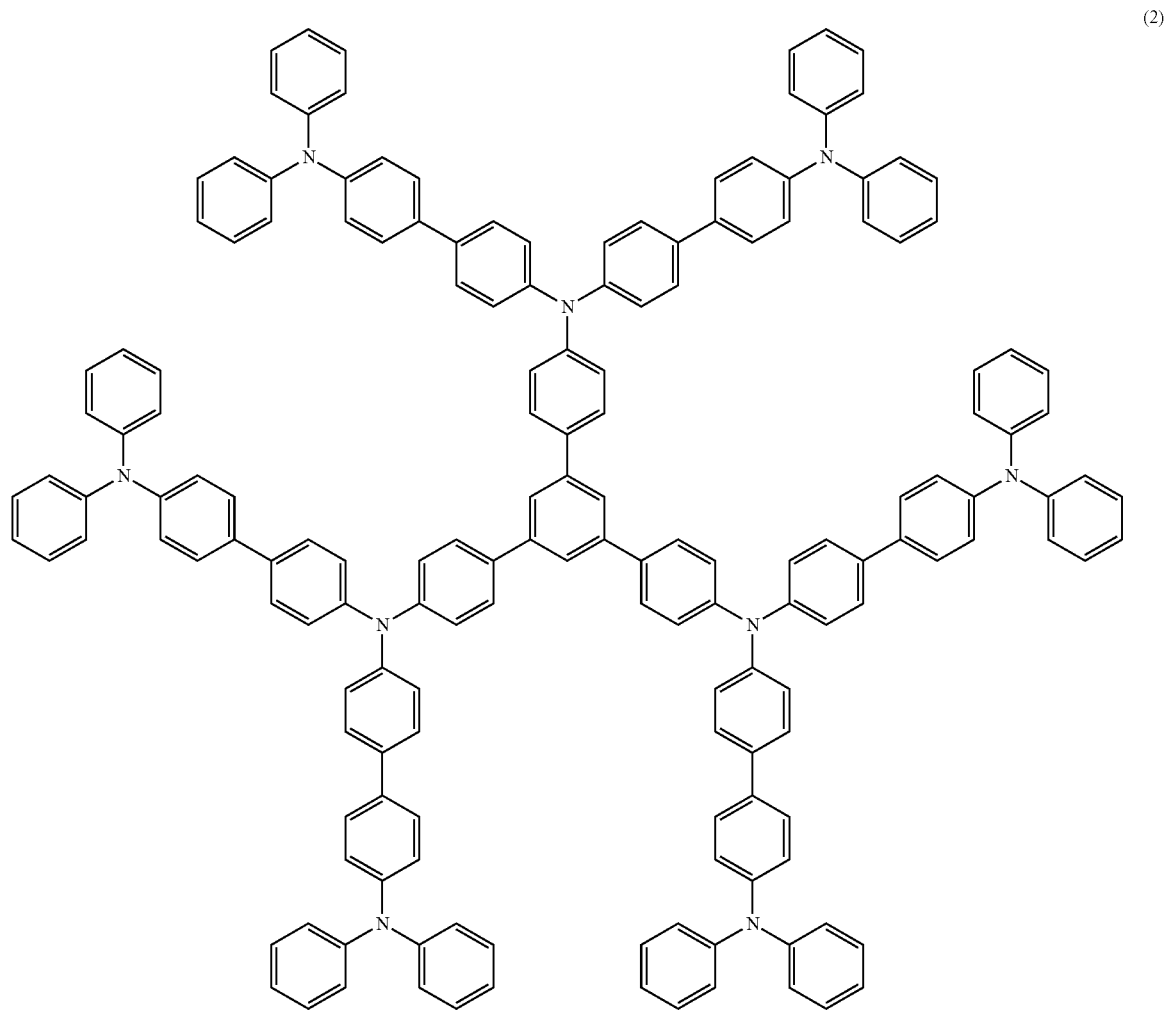
(2)

[Chem. 3]
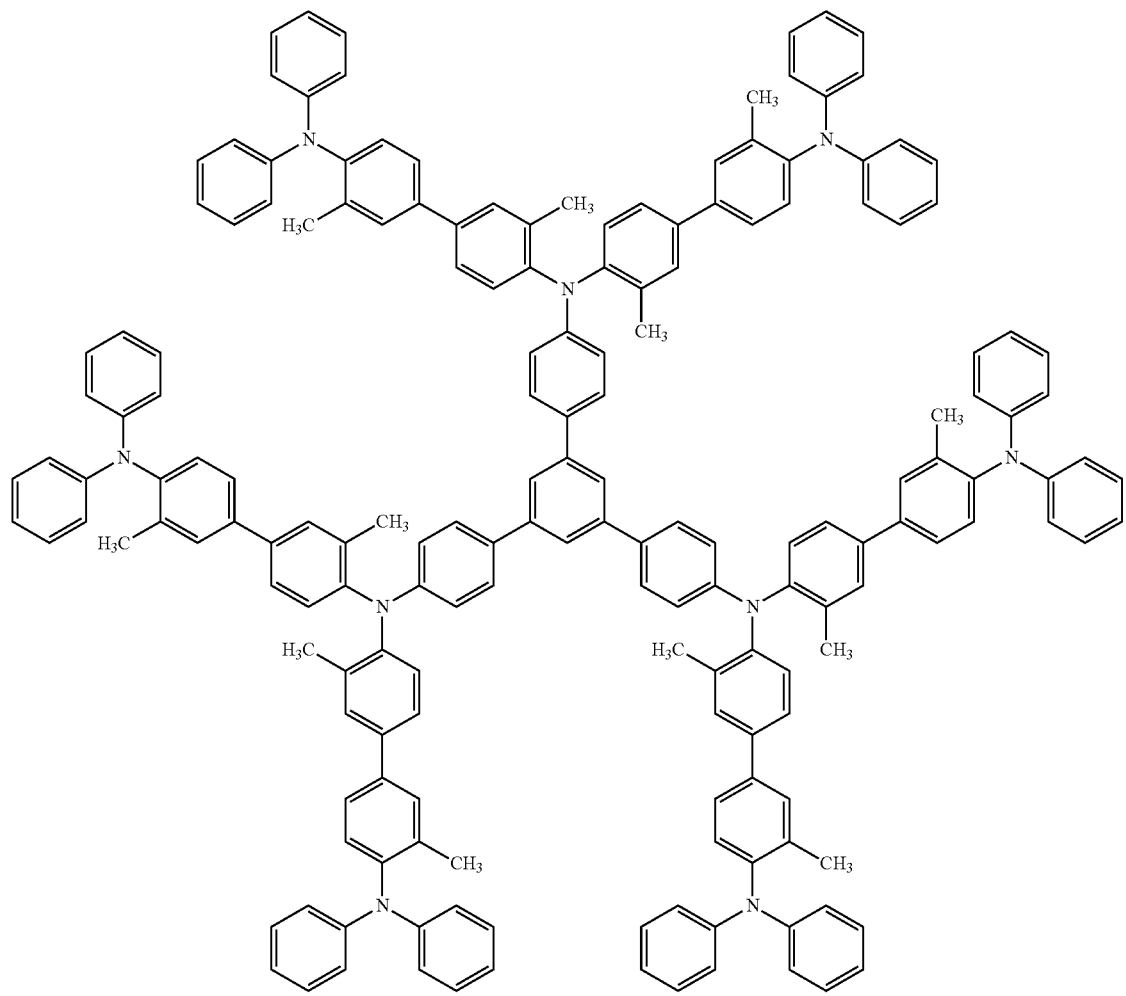
(3)

-continued
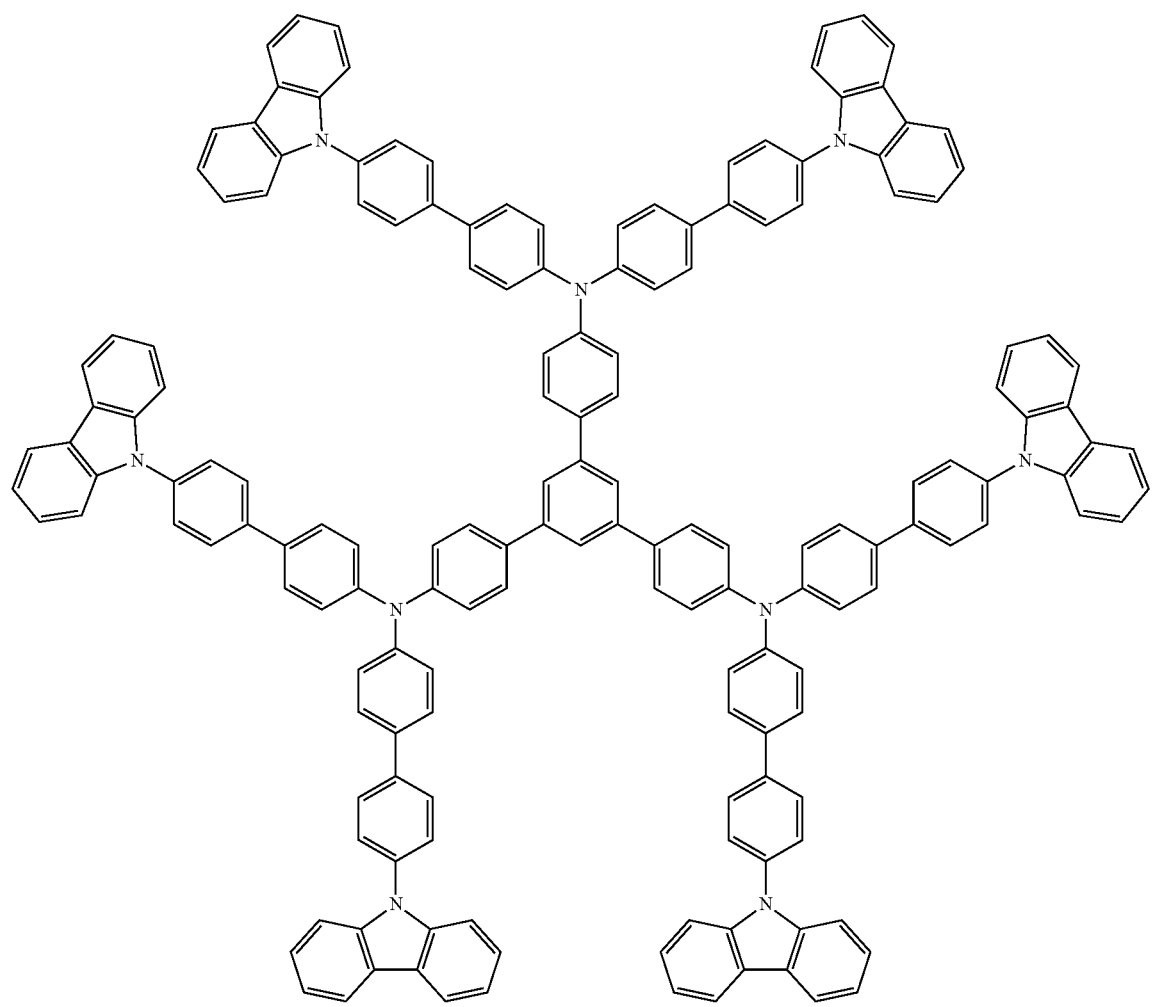
(4)

[Chem. 5]
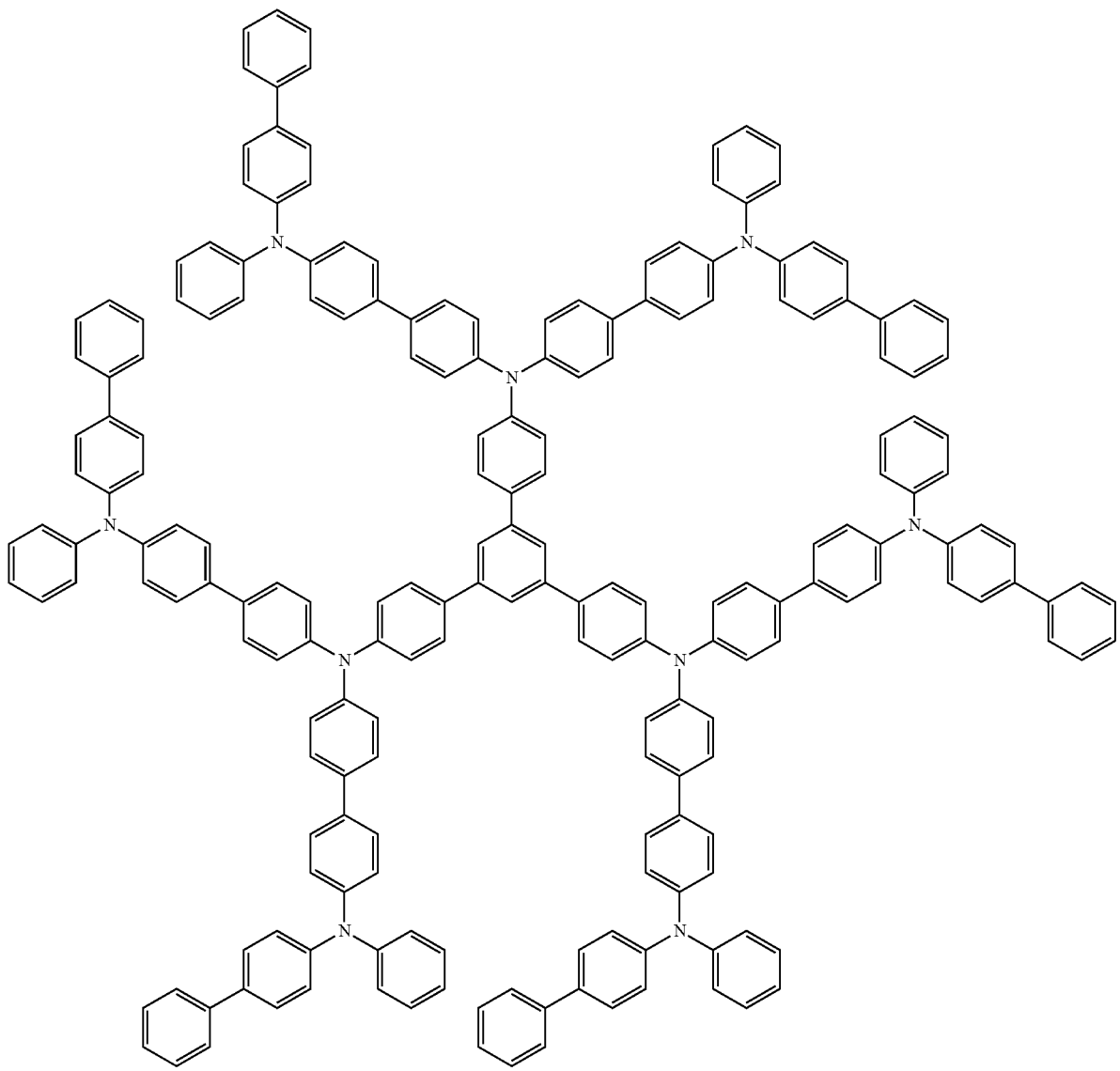
(5)

-continued
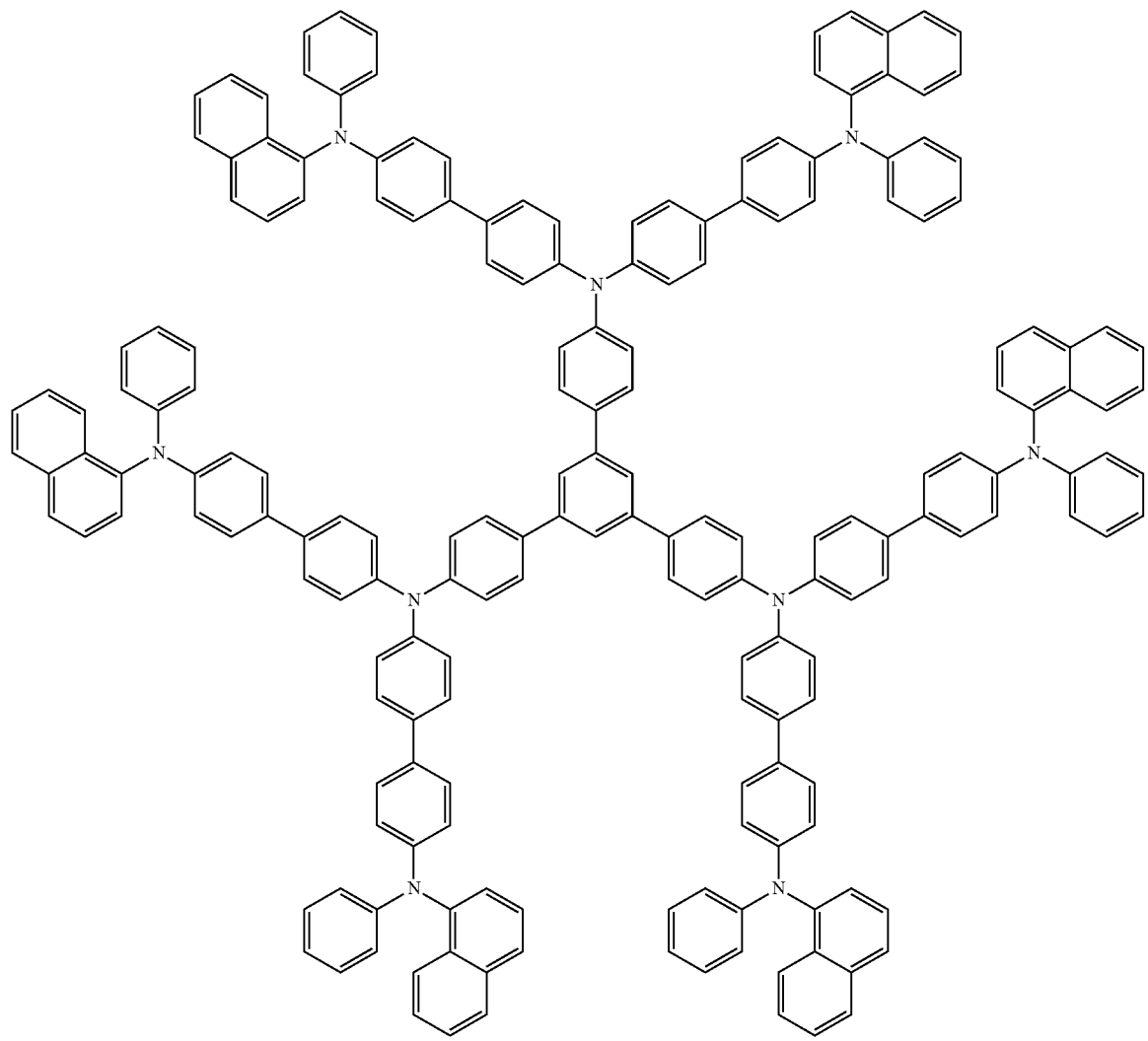
(6)

[Chem. 7]
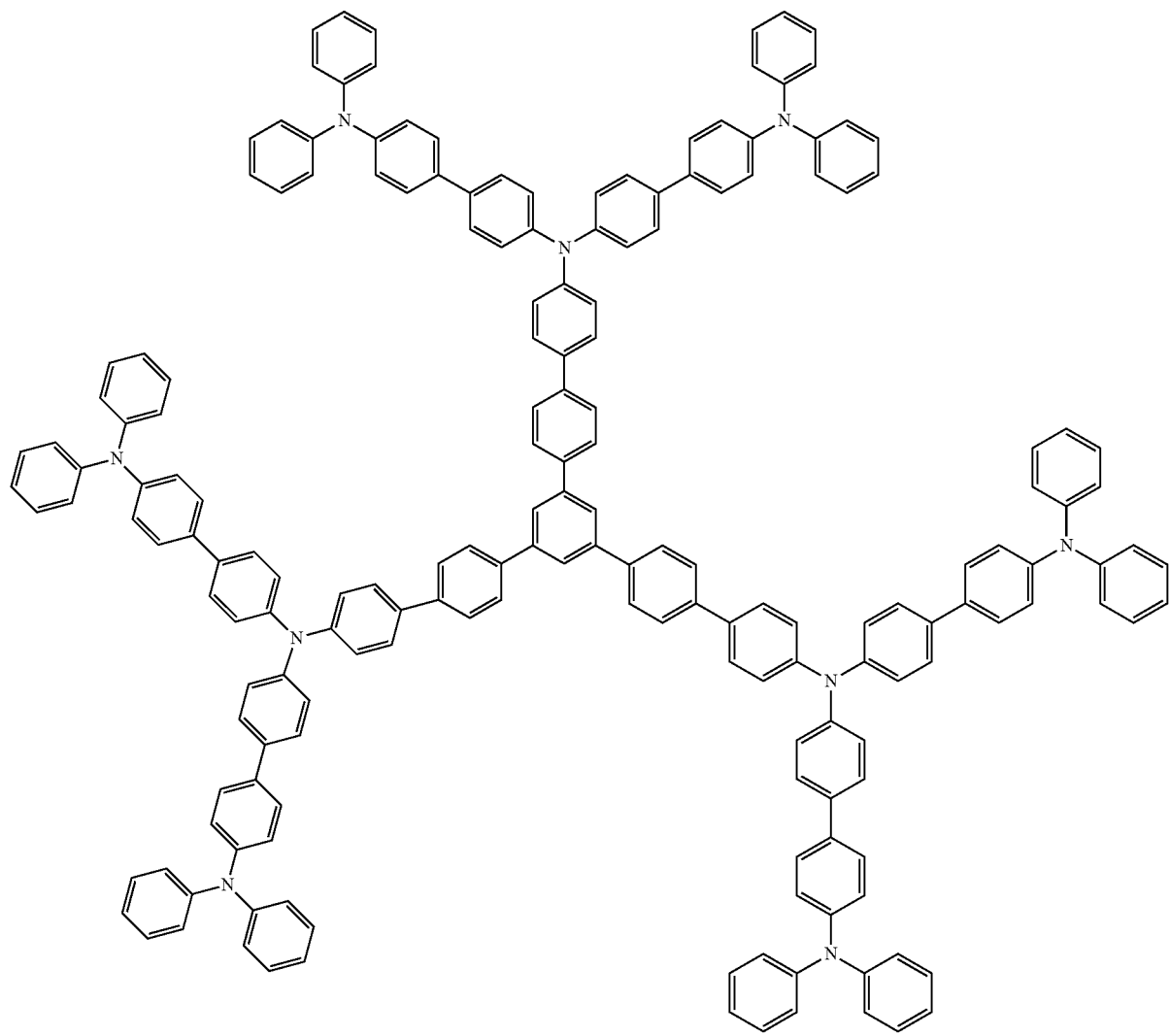
(7)

[Chem. 8]
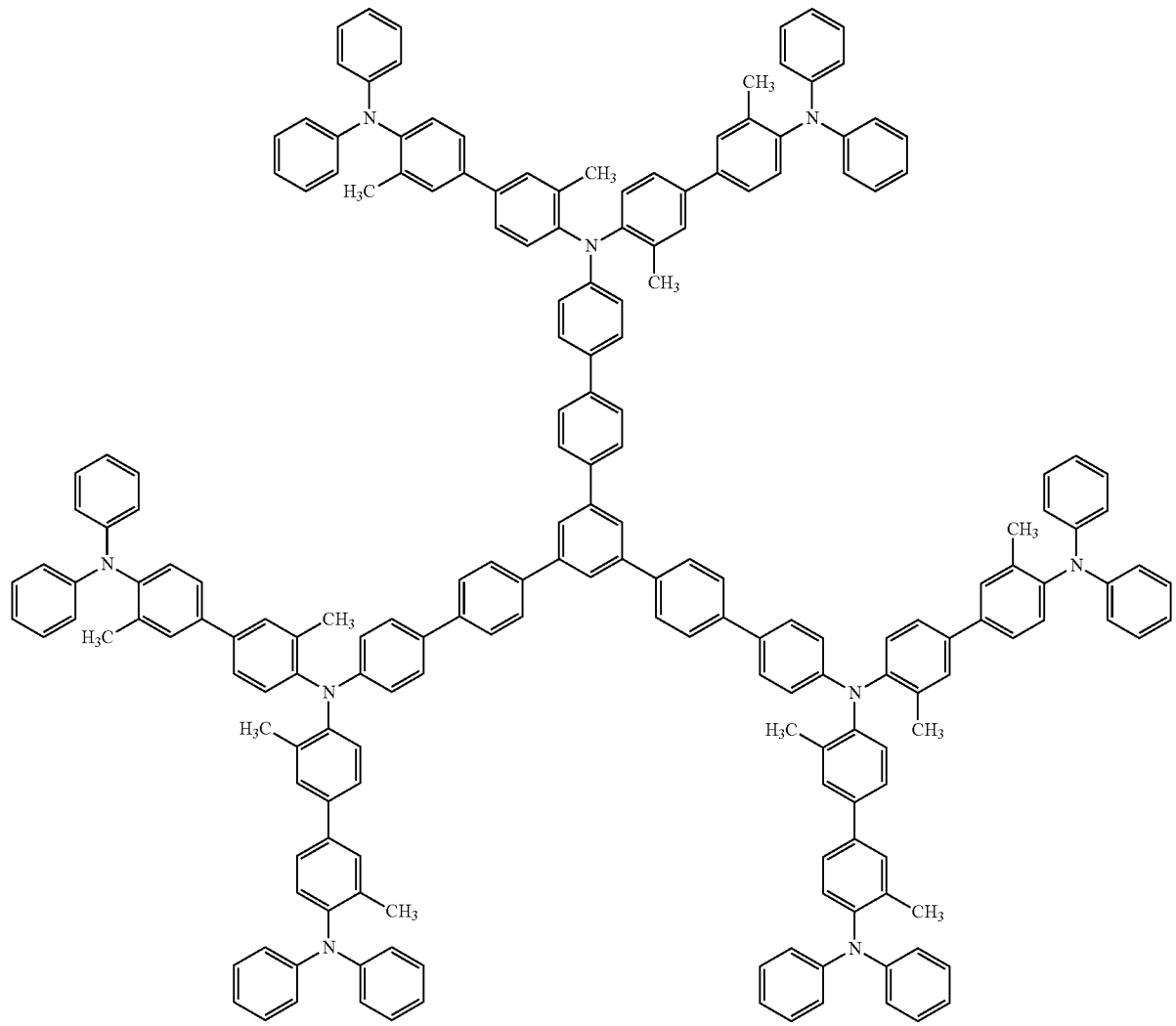
(8)

-continued
[Chem. 9]
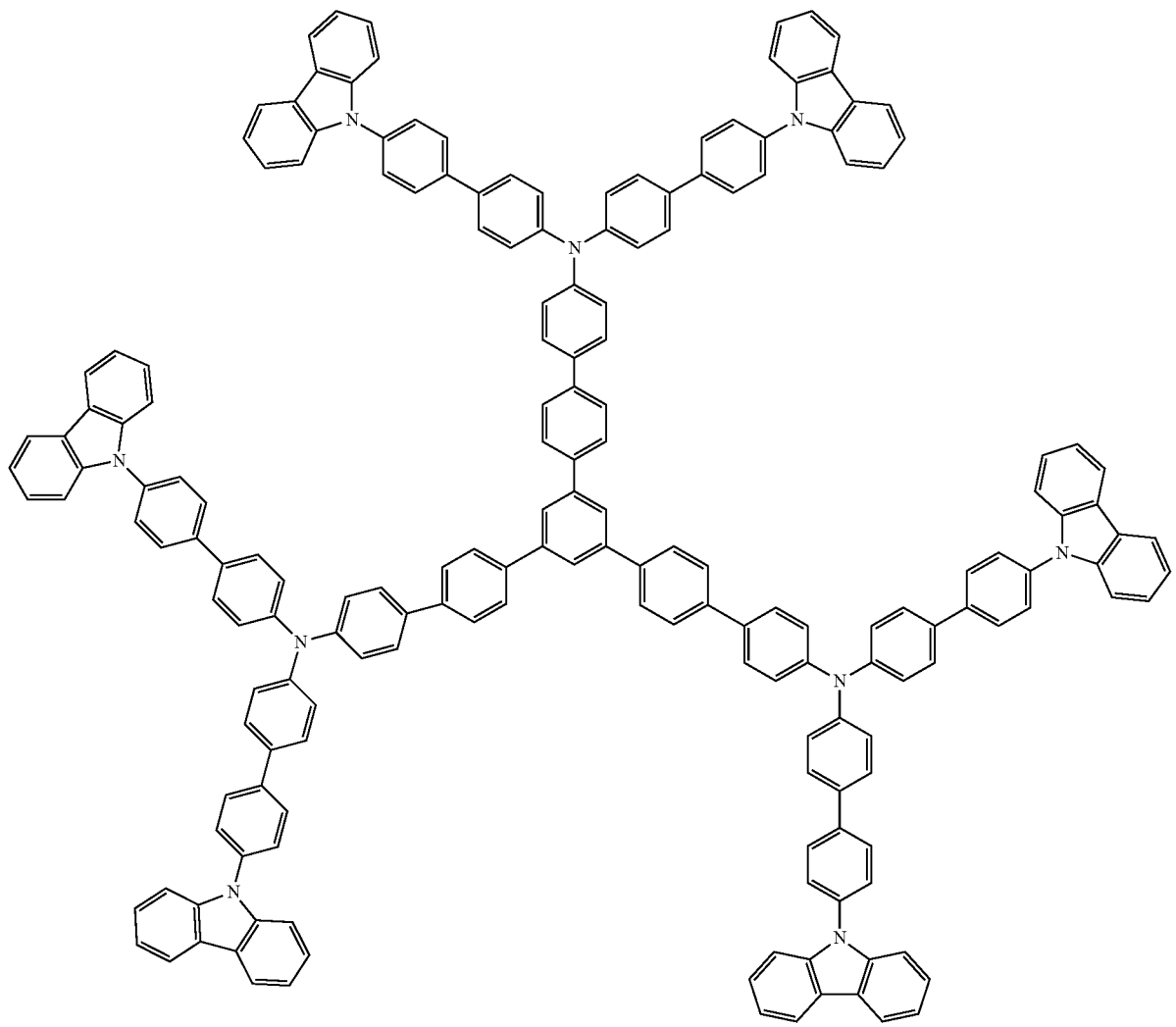
(9)

[Chem. 10]
(10)
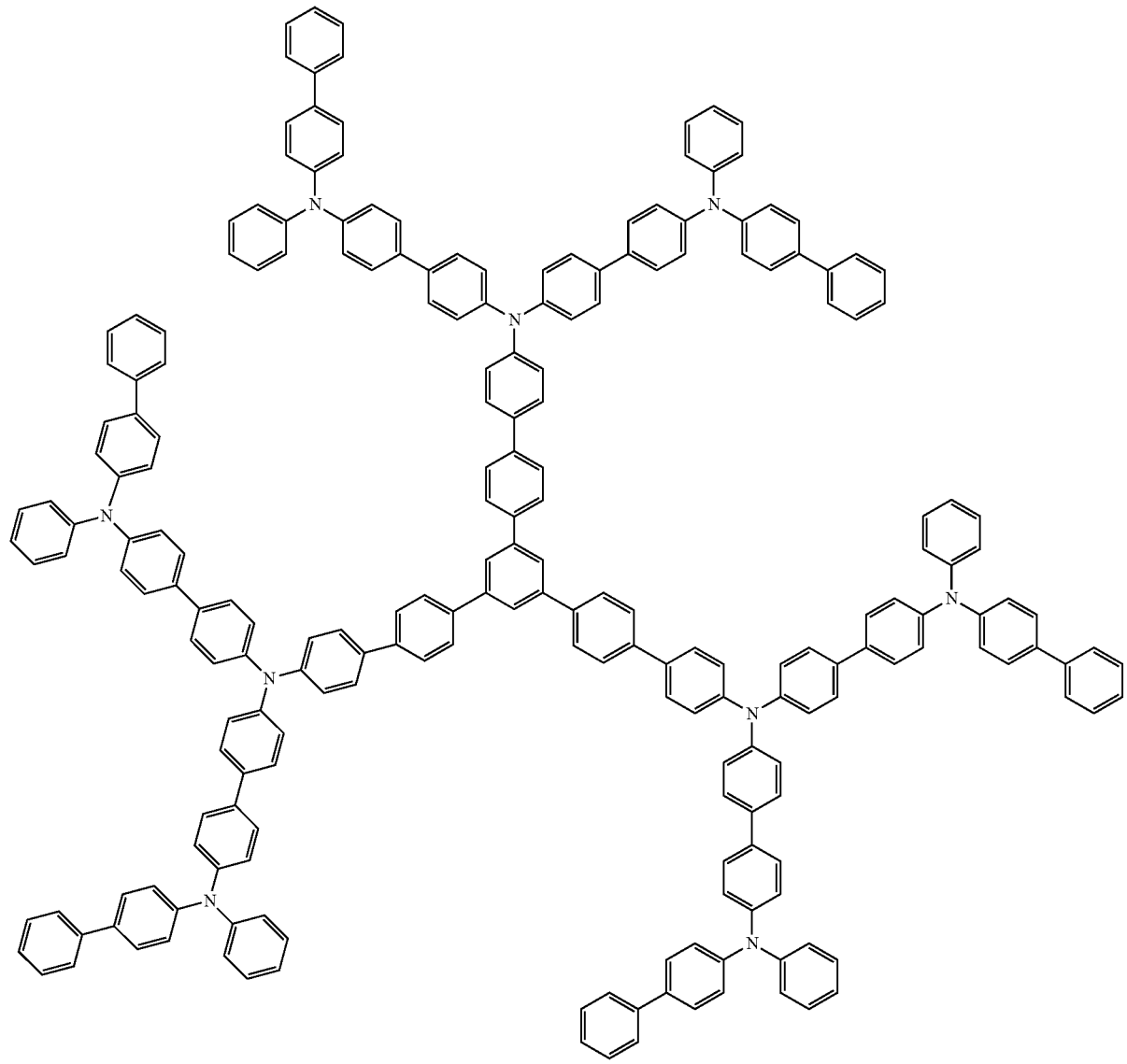

[Chem. 11]
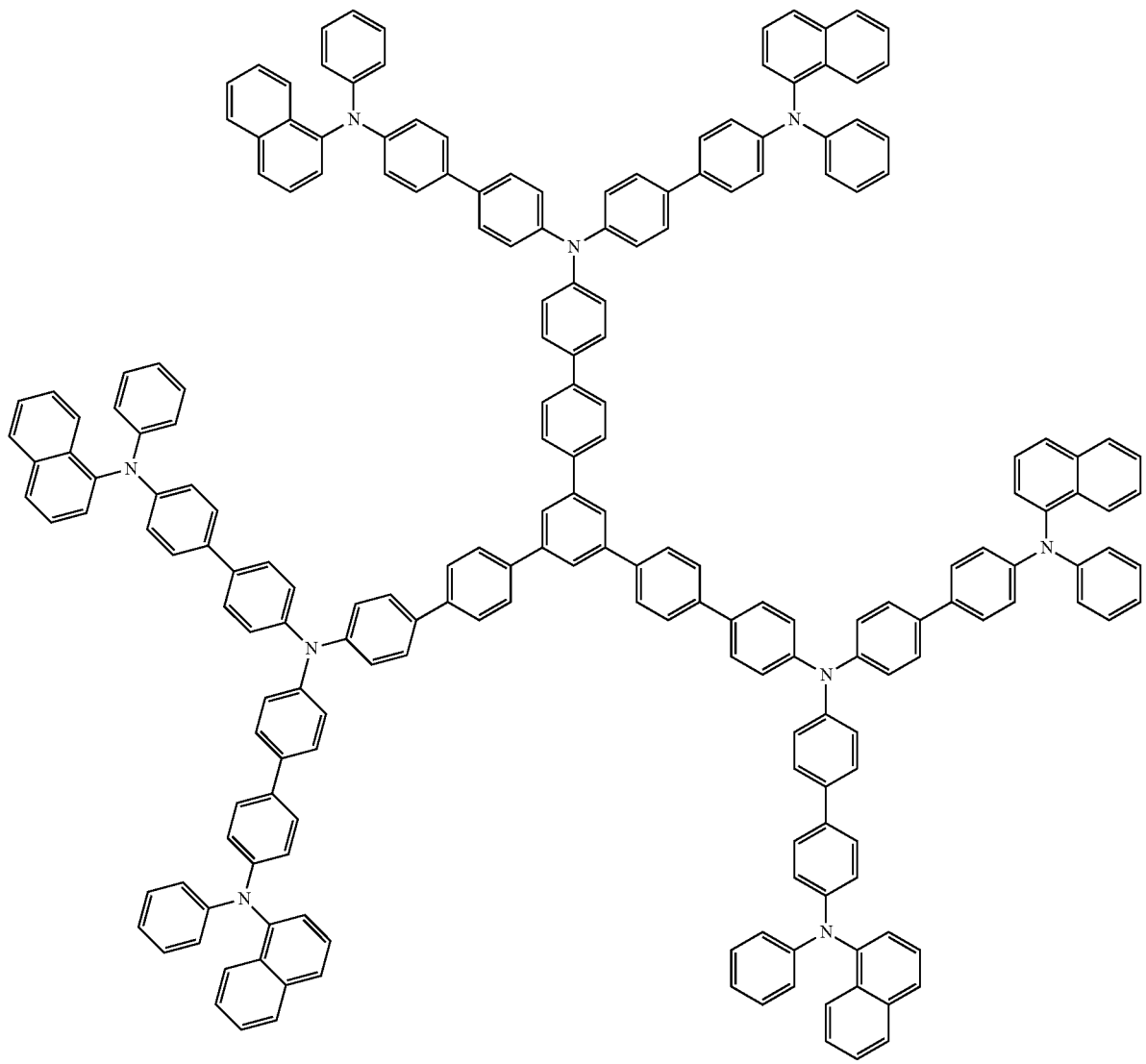
(11)

[Chem. 12]
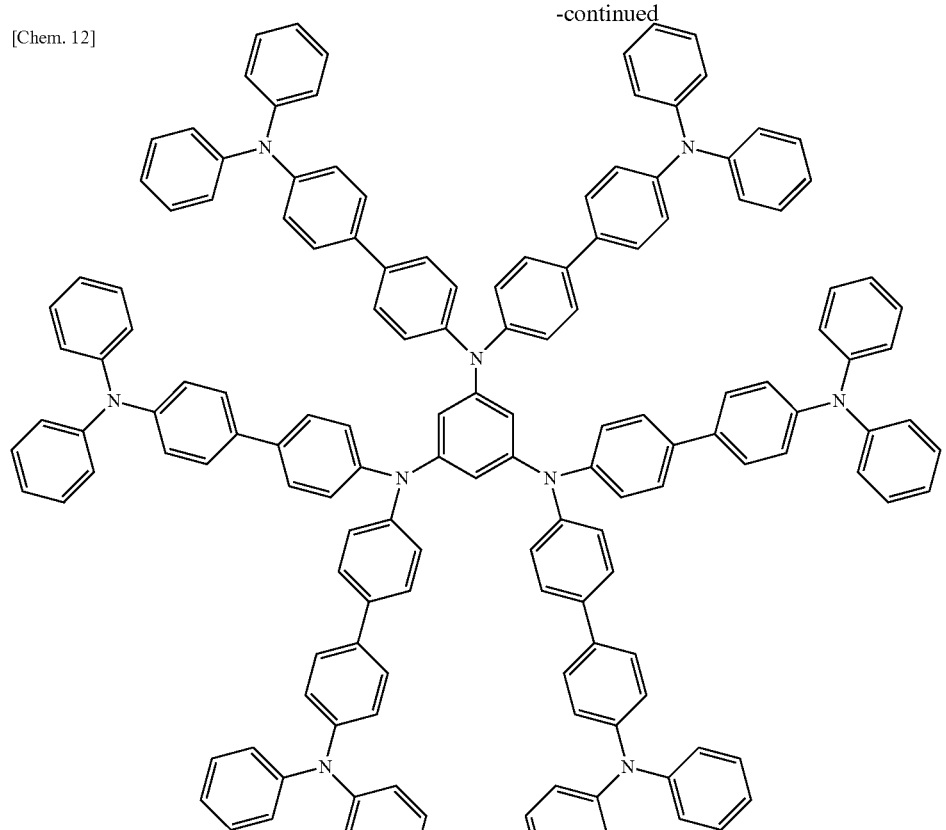
(12)
[Chem. 13]
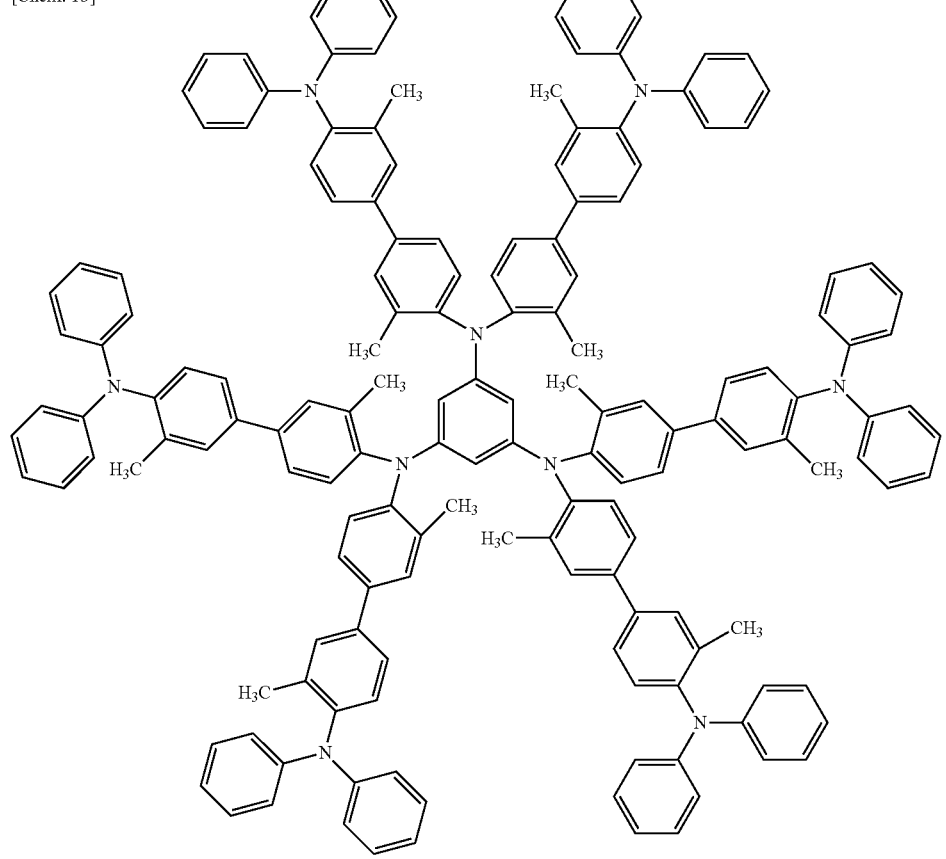
(13)

[Chem. 14]
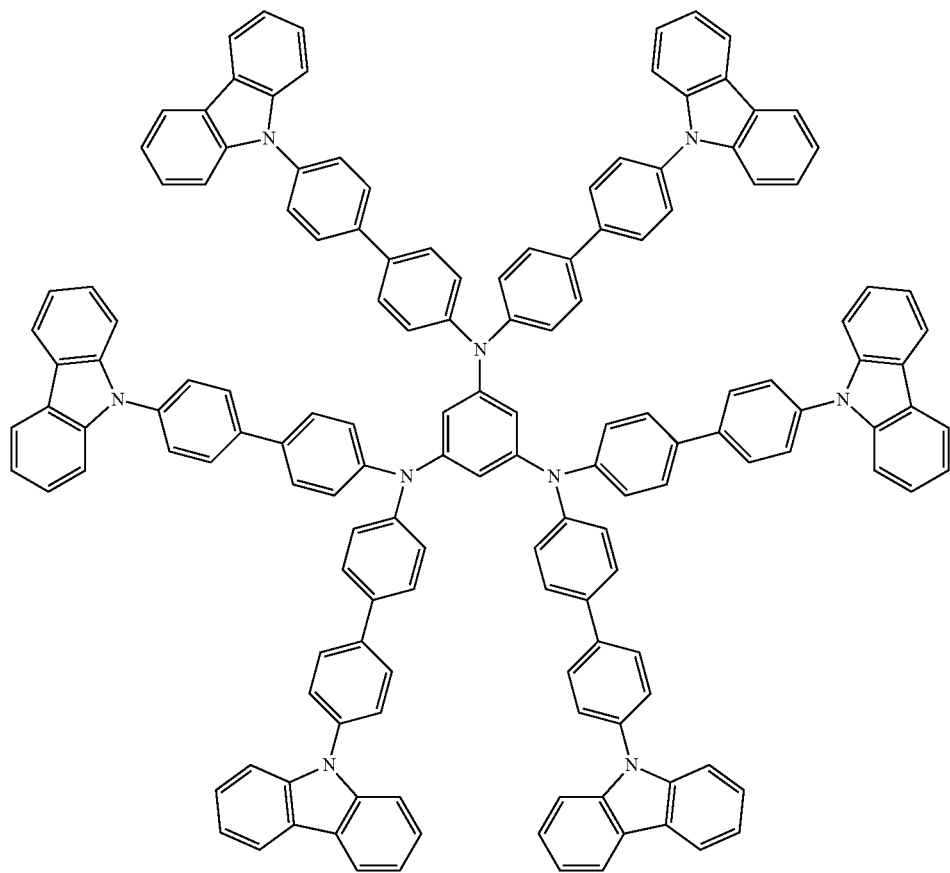
(14)

[Chem. 15]
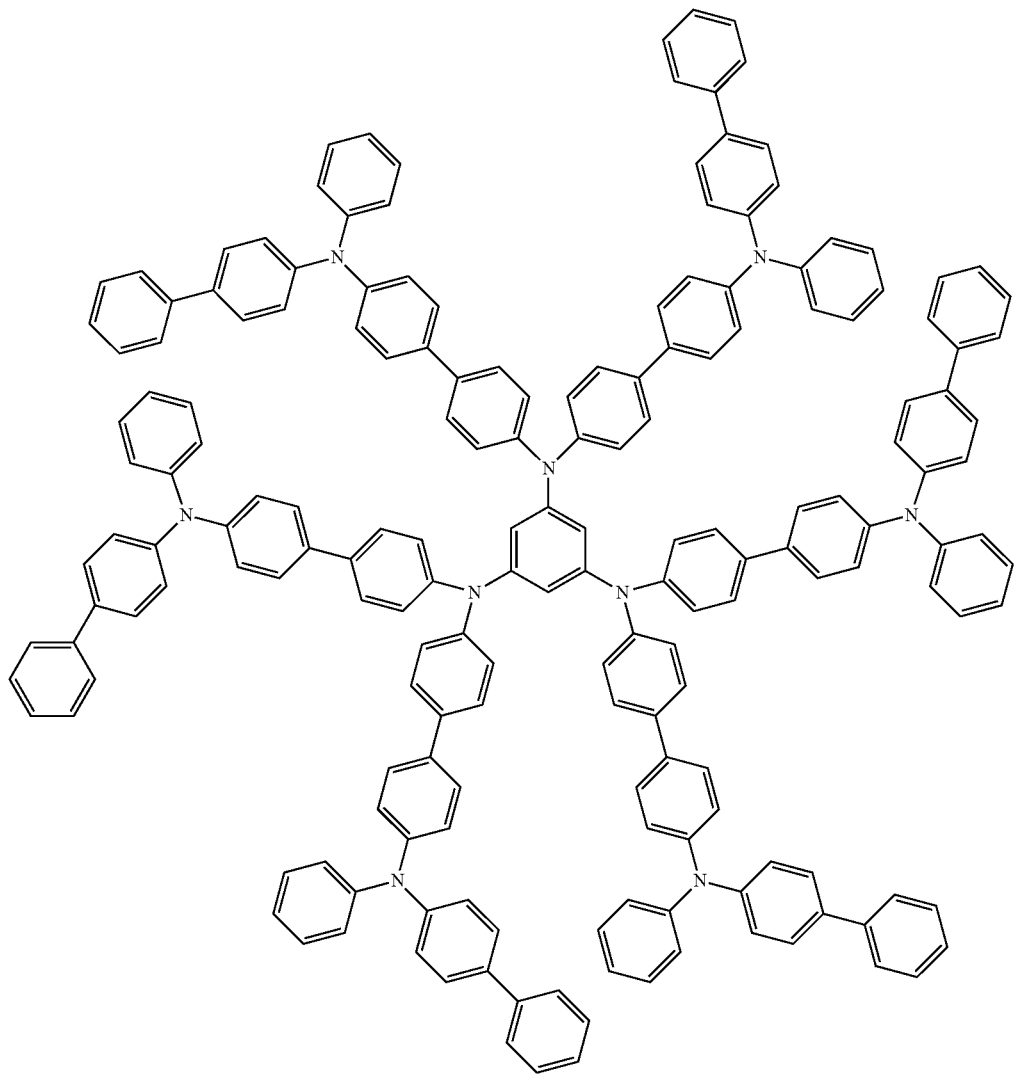
(15)

[Chem. 16]

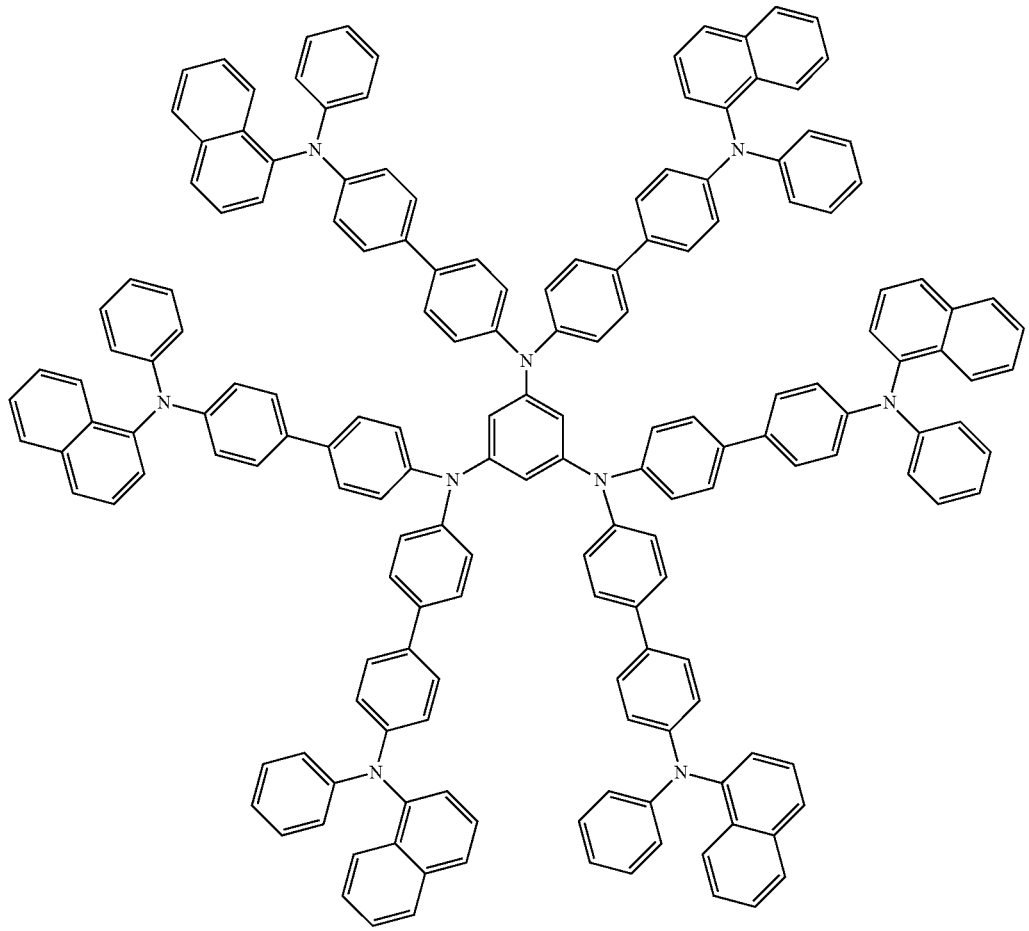

(16)

Purification of the compound of this invention was performed by purification by column chromatography, recrystallization by a solvent, a crystallization method, or the like. The structure of the compound was identified by elemental analysis and the like.

From the compound of this invention, it is possible to easily prepare a coating liquid by using an ordinary solvent. As the solvent to be used for preparing the coating liquid, hydrocarbon such as toluene and xylene; ketone such as cyclohexanone; an amine-based solvent such as anisole; and a chlorine-based solvent such as o-dichlorobenzene and 1,1,2,2-tetrachloroethane are suitable. A functional compound such as an electron injection material, a luminescent material, and electron transport material may be blended into the coating liquid.

The coating liquid of the compound of this invention can form a thin film through coating to prepare an organic EL device. As the film formation method using the coating liquid, a coating method such as spin coating, casting, micro-gravure coating, gravure coating, bar coating, roll coating, wire bar coating, dip coating, spray coating, screen printing, flexographic printing, offset printing, inkjet printing may be employed.

The thickness of the coating film may be selected so as to optimize a driving voltage and durability of the organic EL device. At least a thickness that prevents current leakage is required, but too large thickness is not preferred because the driving voltage of the organic EL device is undesirably increased. Accordingly, the film thickness of the coating film is, for example, 1 nm to 1 μm, and preferably 10 to 100 nm.

Examples of the structure of the organic EL device include a structure having an anode, a hole injection/transport layer, a luminescent layer-cum-electron transport layer, an electron injection layer, and a cathode, which are provided in this order on a substrate; and a structure having an anode, a hole injection layer, a hole transport layer, a luminescent layer, an electron transport layer, an electron injection layer, and a cathode, which are provided in this order on a substrate. The electron injection layer may be omitted.

In such multilayer structures, it is possible to further increase the number of layers, for example, by providing an electron blocking layer between the hole transport layer and the luminescent layer, or by providing a hole blocking layer between the luminescent layer and the electron transport layer. To the contrary, it is possible to reduce the number of organic layers by allowing one layer to serve as functions of several organic layers in combination, such as the case of a hole injection layer-cum-hole transport layer-cum-luminescent layer-cum-electron transport layer.

As the anode of this invention, an electrode material having a large work function such as ITO, NESA, and tin oxide may be used. As the hole injection/transport layer, the arylamine compound having a molecular weight of 1,500 to 6,000 of this invention is used. The compound of this invention may be used as the hole transport layer and combined with a hole injection layer using another material or may be used as the hole injection layer and combined with a hole injection layer using another material, to prepare an organic EL device.

As the hole injection layer to be used in combination, those obtained by vapor deposition of a material such as copper phthalocyanine (hereinafter abbreviated as CuPc), a triphenylamine derivative of starburst type, and a naphthaleneamine compound may be used. Alternatively, a coating film of a polymer material or a coating film that has undergone a treatment for the purpose of coating film insolubilization may be used. Examples of the polymer material include PEDOT/PSS, a polymerizable polymer having a hole-transporting aromatic amine at a side chain or a main chain, and the like. Examples of the treatment include ultraviolet ray irradiation, a heat treatment.

As the hole transport layer to be used in combination, a hole transport material such as N,N'-diphenyl-N,N'-di(α-naphthyl)benzidine (hereinafter abbreviated as NPD) may be used.

As the luminescent layer or the electron transport layer of this invention, those obtained by mixing the arylamine compound of this invention with a luminescent material or an electron transport material and those obtained by mixing a polymer material with an electron transport material may be used. Examples of the polymer material include a polydialkylfluorene derivative, PVK, polyaniline, polythiophene, poly (p-phenylenevinylene), polysiloxane, and the like. Also, various luminescent materials, and electron transport materials such as a carbazole derivative, an aluminum complex of quinoline, a tetravalent metal complex of quinoline, an oxazole derivative, and a phenanthroline derivative may be used.

Also, it is possible to enhance the performance of the organic EL device of this invention by adding, to the luminescent layer, a luminescent material referred to as a dopant including fluorescent dyes such as quinacridone, coumarin 6 and rubrene, and phosphorescent materials such as an iridium complex of phenylpyridine, or by adding an electron transport material such as an oxazole derivative and a triazole derivative.

As the electron injection layer of the organic EL device of this invention, lithium fluoride, cesium, and the like may be used. As the cathode of this invention, an electrode material having a small work function, including metals such as magnesium, calcium and aluminum and alloys of one or more of the metals and silver, indium or the like may be used.

The organic EL device of this invention may have a hole blocking layer. As the hole blocking layer, bathocuproin, an oxazole derivative, a triazole derivative, and the like may be used.

Embodiments of the present invention will be illustrated in greater detail with reference to the following Examples, but the invention should not be construed as being limited thereto so long as not exceeding the gist thereof.

EXAMPLE 1

Synthesis of 1,3,5-tris{4-[N,N-bis(4'-diphenylamino-biphenyl-4-yl)]aminophenyl}benzene (hereinafter abbreviated as TAP9-2) (2)

Under a nitrogen gas stream, 50 ml of dehydrated toluene, 8.33 g of N,N-bis(4'-diphenylaminophenyl-4-yl)amine, 1.68 g of 1,3,5-tris(4-bromophenyl)benzene, 1.77 g of sodium tertiary butoxide, and 0.01 g of palladium acetate (II) were added and heated to 60° C., followed by adding 0.036 g of tritertiary butylphosphine to allow a reaction for 9 hours under reflux.

After completion of the reaction, the mixture was left to cool at a room temperature, followed by filtration, collection, and air drying of a precipitate. Washing with 100 ml of water and filtration of the thus-collected solid was repeated (these operations were conducted twice), and then washing with 100 ml of methanol and filtration was conducted. After washing the solid with toluene by heating to reflux, a crude product was obtained by cooling, filtration, and collection. The thus-obtained crude product was dissolved into 1,2-dichlorobenzene by heating to remove insoluble matters by filtration, and then the 1,2-dichlorobenzene solution was added to methanol to precipitate a crystal, followed by filtration. The crystal was subjected to recrystallization using 1,2-dichlorobenzene repeatedly to obtain 4.2 g of TPA9-2 (yield: 60%) of high purity. An HPCL purity of TPA9-2 obtained by the above operation was 99.5%.

Elemental analysis of the obtained slightly yellowish white powder was conducted. Measurement results of the elemental analysis are as follows.

Theoretical value (carbon: 88.97%) (hydrogen: 5.47%) (nitrogen: 5.56%)

Actual measurement value (carbon: 88.64%) (hydrogen: 5.67%) (nitrogen: 5.50%)

The obtained compound was analyzed by using MALDI-TOF-MS (Perspective Biosystem Inc., Functional Polymer Department in Fiber Faculty of Shinshu University) which is a mass analysis apparatus. From measurement results of TOF-MS, it was confirmed that TPA9-2 has a molecular weight that is equal to the theoretical value, i.e. 2,267. From the above results, the compound of this invention was identified.

COMPARATIVE EXAMPLE 1

In order to prove that the compound of JP-A-8-49045 has the characteristic of being hardly soluble to organic solvents, 1,3,5-tris[4-(dibiphenylamino)phenyl]benzene (hereinafter abbreviated as TBAPB) which is an arylamine compound having a structure similar to that of Compound (2) of Example 1 and having a molecular weight of 1,264:

[Chem. 17]

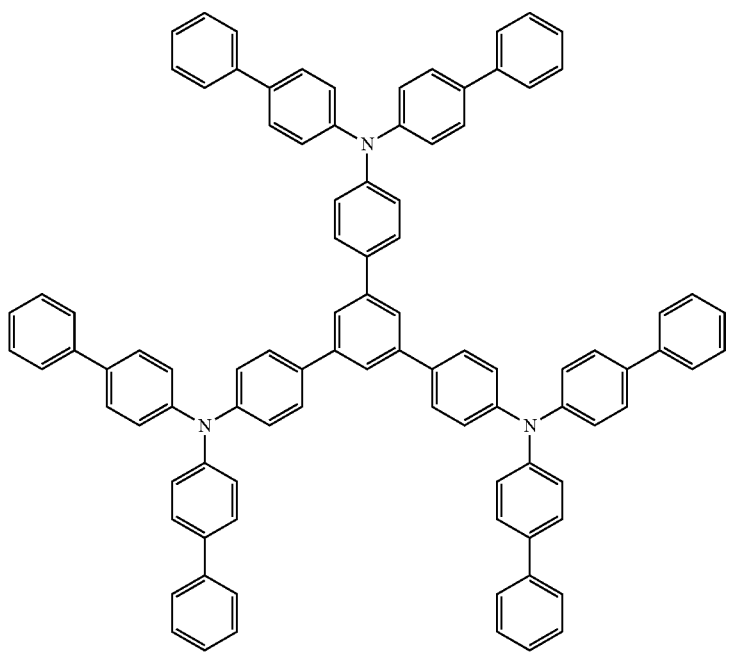

(17)

was synthesized as a compound of Comparative Example 1.

Synthesis of 1,3,5-tris[4-(dibiphenylamino)phenyl]benzene (17)

Under a nitrogen gas stream, 120 ml of dehydrated toluene, 7.8 g of 4-dibiphenylamine, 4.0 g of 1,3,5-tris(4-bromophenyl)benzene, 3.2 g of sodium tertiary butoxide, and 0.02 g of palladium acetate (II) were added and heated to 60° C., followed by adding 0.07 g of tritertiary butylphosphine to allow a reaction for 5 hours under reflux.

After completion of the reaction, the mixture was left to cool at a room temperature, followed by filtration, collection, and air drying of a precipitate. The collected solid was washed with 100 ml of water, filtered, and dried to obtain a crude product. The crude product was dissolved into 1,2-dichlorobenzene by heating to remove an insoluble catalyst residue by hot filtration, and then the filtrate was left to cool at a room temperature to precipitate a crystal, followed by filtration and collection of the crystal. The crystal was repeatedly subjected to purification by recrystallization using 1,2-dichlorobenzene to obtain 4.8 g of TBAPB (yield: 52%).

The chemical structure of the obtained white powder was identified by elemental analysis. Measurement results of the elemental analysis are as follows.

Theoretical value (carbon: 91.17%) (hydrogen: 5.51%) (nitrogen: 3.32%)

Actual measurement value (carbon: 91.16%) (hydrogen: 5.66%) (nitrogen: 3.36%)

EXAMPLE 2

Glass transition points of Compound (2) of Example 1 and Compound (17) of Comparative Example 1 were determined by using a differential scanning calorimeter (product of Seiko Instruments Inc.). Measurement results are as follows.

Compound (2) of Example 1: glass transition point of 177° C.

Compound (17) of the Comparative Example 1 had low amorphousness and did not exhibit an endothermic phenomenon of transitioning to a glass phase during a temperature-raising stage after melting and quenching. From the above results, it is apparent that the compound of this invention has higher amorphousness than the compound of JP-A-8-49045, and that the state of the thin film formed therefrom is stable.

EXAMPLE 3

2 mg of Compound (2) of Example 1 of this invention was placed into a beaker, and 1.0 g of cyclohexanone was added thereto, followed by mixing with stirring using a magnetic stirrer. After confirming that the compound was perfectly dissolved, the mixture was filtrated by using a 0.2 μm filter to prepare 1 ml of 2 mass %-coating liquid.

COMPARATIVE EXAMPLE 2

Attempts were made for dissolving Compound (17) of Comparative Example 1 of this invention by using various solvents such as cyclohexanone, xylene, THF, chloroform, and 1,1,2,2-tetrachloroethane, but the compound was not dissolved to fail to obtain a solution having a concentration of 0.7 mass % or more.

It was impossible to prepare a coating liquid for producing an organic EL device from Compound (17) of Comparative Example 1 although Compound (17) has a molecular weight that is ¼ of Compound (2) of Example 1. From the above results, it is apparent that the compound of JP-A-8-49045 is not suitable for production of wet-process type device.

EXAMPLE 4

The coating liquid of Compound (2) of Example 1 of this invention, which was prepared in Example 3, was coated on a glass plate by spin coating, followed by drying in a vacuum oven at 100° C. to obtain a coating film of about 50 nm.

By using an atomic force microscope (hereinafter abbreviated as AFM) (SPA-400; product of SII Nanotechnology Inc.), the surface state of the formed coating film was observed. The coating film of the compound of Example 1 of this invention was a thin film that is uniform and defect-free. The flatness of the coating film was high, and a calculated average roughness (Ra) in surface roughness measurement was 0.25 nm.

EXAMPLE 5

The work function of the coating film of Compound (2) of Example 1 formed on the glass plate was measured by using an atmospheric photoelectron spectrometer (AC2; product of Riken Keiki Co., Ltd.). The work function was 5.32 eV.

From the above results, the thin film formed by using the arylamine compound having a molecular weight of 1,500 to 6,000 of this invention is considered to have an appropriate energy level as the hole injection/transport layer.

EXAMPLE 6

An organic EL device was produced by stacking, on a glass substrate 1 on which an ITO electrode had been formed as a transparent anode 2, a hole injection/transport layer 3, a luminescent layer-cum-electron transport layer 4, an electron injection layer 5, a cathode (aluminum electrode) 6.

The glass substrate 1 on which an ITO film having a film thickness of 150 nm had been formed was washed with an organic solvent and then subjected to washing of its surface by an oxygen plasma treatment.

The coating liquid prepared in Example 3 of Compound (2) of Example 1 was coated on the ITO substrate by spin coating, followed by drying in a vacuum oven at 100° C. to obtain the hole injection/transport layer 3 of about 50 nm. The film was attached to a vacuum vapor deposition machine, and a pressure was reduced to 0.001 PA or less.

Subsequently, about 50 nm of Alq was formed as the luminescent layer-cum-electron transport layer 4 at a deposition speed of 0.6 angstrom/s. Next, about 0.5 nm of lithium fluoride was formed as the electron injection layer 5 at a deposition speed of 0.1 angstrom/s. Lastly, with inserting a mask for cathode vapor deposition, about 200 nm of aluminum was deposited to form the cathode 6. The vapor deposition performed until this step was conducted successively without breaking vacuum. The produced device was stored in a vacuum desiccator, and characteristic measurement was performed in an atmosphere under an ordinary temperature.

The thus-obtained organic EL device of this invention was evaluated in terms of a luminescent efficiency defined by luminance of luminescence/current amount and a power efficiency defined by illuminance of luminescence/electric energy, each at luminescence of 5,000 cd/m$^2$ and luminescence of 10,000 cd/m$^2$.

The organic EL device generated stable green luminescence. The luminescence efficiencies were 4.31 and 4.37 and the power efficiencies were 1.60 and 1.49, each at the luminescence of 5,000 cd/m$^2$ and the luminescence of 10,000 cd/m$^2$, respectively.

A maximum luminance before breakthrough was evaluated by increasing the load of the current density by increasing the driving voltage. Since the maximum luminance measured by the method reflects electrical stability of the device, the maximum luminance serves as an index for durability of the organic EL device.

When the driving voltage was raised, the organic EL device exhibited the maximum luminance of 34,100 cd/m$^2$ at 11.1 V, and then device deterioration began to diminish the luminance.

COMPARATIVE EXAMPLE 3

The material of the hole injection/transport layer 3 was replaced by PVK for the purpose of comparison, and the characteristics thereof were examined. A coating liquid was prepared in the same manner as in Example 3 except for conducting the coating liquid preparation by dissolving PVK into orthodichlorobenzene. The hole injection/transport layer 3 was formed by coating in the same manner as in Example 6. Subsequently, in the same manner as in Example 6, a luminescent layer-cum-electron transport layer 4, an electron injection layer 5, and a cathode 6 were each formed by vapor deposition.

The organic EL device obtained by using PVK generated stable green luminescence. The luminescence efficiencies were 4.20 and 3.80 and the power efficiencies were 1.57 and 1.33, each at the luminescence of 5,000 cd/m$^2$ and the luminescence of 10,000 cd/m$^2$, respectively. Under a high current driving condition exceeding a luminance of luminescence of 6,000 cd/m$^2$, deterioration in efficiency was observed.

From the above results, it can be concluded that the organic EL device of this invention has better stability in luminescence characteristics than the device obtained by using PVK upon luminescence at high luminance exceeding 6,000 cd/m$^2$.

When the load was increased by raising the voltage, the device exhibited a maximum luminance of 17,300 cd/m$^2$ at 10.1 V and then started to deteriorate. The maximum luminance before breakthrough was ½ of that of the organic EL device of Example 6.

From the above results, the organic EL device of this invention has higher electrical stability and better durability than the device obtained using PVK.

EXAMPLE 7

Figure 3:
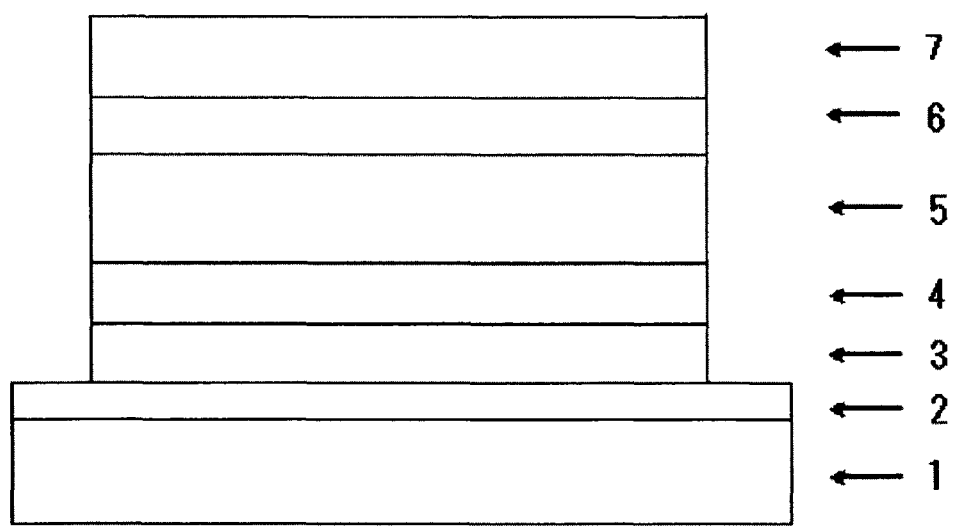
FIG. 3 is a diagram showing the EL device structure of Example 7.

As shown in FIG. 3, the organic EL device was produced by stacking, on a glass substrate 1 on which an ITO electrode had been formed as a transparent anode 2, a hole injection layer 3, a hole transport layer 4, a luminescent layer-cum-electron transport layer 5, an electron injection layer 6, a cathode (aluminum electrode) 7 in this order.

The glass substrate 1 on which ITO having a film thickness of 150 nm had been formed was washed with an organic solvent and then subjected to washing of its surface by an oxygen plasma treatment.

The hole injection layer 3 was formed on the ITO substrate by vapor-depositing about 15 nm of CuPC at a vapor deposition rate of 6 nm/min by using a vacuum vapor deposition machine. The ITO substrate was taken out after pressure reduction, and the hole transport layer 4 of about 35 nm was formed on the ITO substrate by coating the coating liquid of Compound (2) of Example 1 prepared in Example 3 on the ITO substrate by spin coating, followed by drying in a vacuum oven at 100° C. The substrate with the hole transport layer 4 was returned to the vapor deposition machine to form about 50 nm of Alq at a vapor deposition rate of 0.6 angstrom/s as the luminescent layer-cum-electron transport layer 5 in the same manner as in Example 6. Next, about 0.5 nm of lithium fluoride was formed at a vapor deposition rate of 0.1 angstrom/s as the electron injection layer 6. Lastly, with inserting a mask for cathode vapor deposition, the cathode 7 was formed by vapor-depositing about 200 nm of aluminum. The thus-obtained device was stored in a vacuum desiccator, and characteristics measurement was conducted in the atmosphere at an ordinary temperature.

The organic EL device produced as described above exhibited stable green luminescence. A luminescence of 5,000 cd/m² was exhibited at a driving voltage of 7.2 V, and a luminescence of 10,000 cd/m² was exhibited at a driving voltage of 7.8 V. The electric efficiencies thereof were 1.49 and 1.45, respectively.

When the driving voltage was further raised, the organic EL device exhibited a maximum luminance of 41,400 cd/m² at 9.5 V, and then device deterioration began to diminish the luminance.

From the above results, it is apparent that the organic EL device of this invention is suitable for high luminance luminescence since it has high electric stability and good durability.

In view of the above results, it is apparent that the arylamine compound having a molecular amount of 1,500 to 6,000 of this invention is a compound having excellent hole injection/transport property and excellent amorphousness. Also, it is apparent that efficiency and durability of the organic EL devices produced by forming a film through coating using the compound of this invention are superior to those of the conventional organic EL devices.

While the present invention has been described in detail and with reference to specific embodiments thereof, it will be apparent to one skilled in the art that various changes and modifications can be made therein without departing from the spirit and scope thereof.

This invention is based on the Japanese patent application No. 2005-251968 filed on Aug. 31, 2005, and the contents thereof are herein incorporated by reference.

INDUSTRIAL APPLICABILITY

The arylamine compound having a molecular weight of 1,500 to 6,000 of this invention is excellent as a compound for organic EL devices, since the compound is formed into a film by coating, achieves a stable thin film state, and has a work function suitable for a hole injection/transport material. By producing an organic EL device using the thin film formed by coating the arylamine compound having a molecular weight of 1,500 to 6,000 of this invention as a hole injection/transport layer or a hole transport layer, it is possible to dramatically improve luminescent efficiency and durability of conventional wet-process type organic EL devices. For example, expansions into utilization for home electric appliances and lighting have been made possible.

The invention claimed is:

1. An arylamine compound having a molecular weight of 1,500 to 6,000 represented by formula (1):

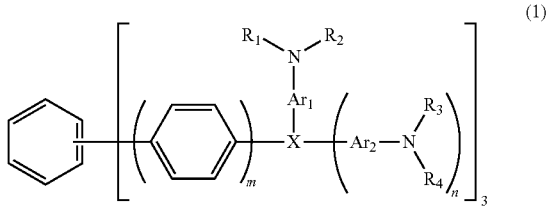

wherein X represents a single bond, CH or $CH_2$, or N or NH; $Ar_1$ and $Ar_2$ are respectively the same and each represents a substituted or unsubstituted phenylene group; $R_1$, $R_2$, $R_3$, and $R_4$ each independently represents a substituted or unsubstituted aryl group wherein said substituent is at least one selected form the group consisting of a fluorine atom, a chlorine atom, a cyano group, a hydroxide group, a nitro group, an alkoxy group, an amino group, a trifluoromethyl group, a naphthyl group, an aralkyl group, a fluorenyl group, an indenyl group, a pyridyl group, a pyrimidyl group, a furanyl group, a pyronyl group, a thiophenyl group, a quinolyl group, a benzofuranyl group, a benzothiophenyl group, an indolyl group, a carbazolyl group, a bezooxazolyl group, a quinoxalyl group, a bezoimidazolyl group, a pyrazolyl group, a dibenzofuranyl group, and a dibenzothiophenyl group, and wherein the aryl group may be substituted by a diarylamine group in such a manner as to form a triphenylamine partial structure, and the aryl group at the terminal may be substituted, by repetition, by a diarylamino group in such a manner as to form a triphenylamine partial structure; m represents an integer of 0 to 2; and n represents 0 or 1.

2. The arylamine compound according to claim 1, wherein the arylamine compound having a molecular weight of 1,500 to 6,000 represented by the formula (1) has 6 or 9 nitrogen atoms in its molecule.

3. The arylamine compound according to claim 2, wherein the arylamine compound having a molecular weight of 1,500 to 6,000 represented by the formula (1) has 9 nitrogen atoms in its molecule.

4. The arylamine compound according to any one of claims 1 to 3, wherein the arylamine compound having a molecular weight of 1,500 to 6,000 represented by the formula (1) has 6 to 9 triphenylamine partial structures in its molecule.

5. The arylamine compound according to claim 1, wherein $R_1$ and $R_3$ of formula (1) represent the same group, and $R_2$ and $R_4$ of formula (1) represent the same group.

6. An organic electroluminescence device comprising a pair of electrodes and at least one organic layer sandwiched therebetween, wherein the device comprises as a constituting material of the at least one organic layer an arylamine compound having a molecular weight of 1,500 to 6,000 represented by formula (1):

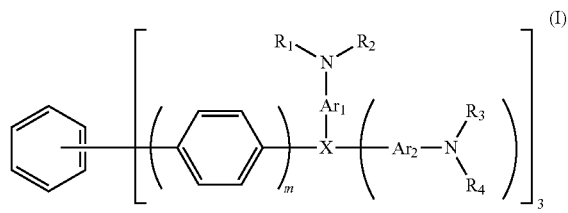

wherein X represents a single bond, CH or $CH_2$, or N or NH; $Ar_1$ and $Ar_2$ are respectively the same and each represents a substituted or unsubstituted phenylene group; $R_1$, $R_2$, $R_3$, and $R_4$ each independently represents a substituted or unsubstituted aryl group wherein said substituent is at least one selected form the group consisting of a fluorine atom, a chlorine atom, a cyano group, a hydroxide group, a nitro group, an alkoxy group, an amino group, a trifluoromethyl group, a naphthyl group, an aralkyl group, a fluorenyl group, an indenyl group, a pyridyl group, a pyrimidyl group, a furanyl group, a pyronyl group, a thiophenyl group, a quinolyl group, a benzofuranyl group, a benzothiophenyl group, an indolyl group, a carbazolyl group, a bezooxazolyl group, a quinoxalyl group, a bezoimidazolyl group, a pyrazolyl group, a dibenzofuranyl group, and a dibenzothiophenyl group, and wherein the aryl group may be substituted by a diarylamine group in such a manner as to form a triphenylamine partial structure, and the aryl group at the terminal may be substituted, by repetition, by a diarylamino group in such a manner as to form a triphenylamine partial structure; m represents an integer of 0 to 2; and n represents 0 or 1.

7. The organic electroluminescence device according to claim 6, wherein the arylamine compound having a molecular weight of 1,500 to 6,000 represented by the formula (1) has 6 or 9 nitrogen atoms in its molecule.

8. The organic electroluminescence device according to claim 7, wherein the arylamine compound having a molecular weight of 1,500 to 6,000 represented by the formula (1) has 9 nitrogen atoms in its molecule.

9. The organic electroluminescence device according to any one of claims 6 to 8, wherein the arylamine compound having a molecular weight of 1,500 to 6,000 represented by the formula (1) has 6 to 9 triphenylamine partial structures in its molecule.

10. The organic electroluminescence device according to claim 6, wherein said at least one organic layer has a film thickness of 1 nm to 1 μm.

11. The organic electroluminescence device according to claim 6, wherein said at least one organic layer has a film thickness of 10 to 100 nm.

12. The organic electroluminescence device according to claim 6, wherein said at least one organic layer functions as a hole injection/transport layer.

* * * * *